(12) United States Patent
Wang et al.

(10) Patent No.: US 6,500,341 B2
(45) Date of Patent: Dec. 31, 2002

(54) PROCESS FOR THE PURIFICATION OF WATER-SOLUBLE NON-IONIC CONTRAST AGENTS

(75) Inventors: Shin-Shin Wang, Hsinchu (TW); Hui-Ping Tsai, Changhua Hsien (TW); Chii-Chang Lai, Taichung Hsien (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 09/941,658

(22) Filed: Aug. 30, 2001

(65) Prior Publication Data

US 2002/0170860 A1 Nov. 21, 2002

(30) Foreign Application Priority Data

May 17, 2001 (TW) ........................................ 90111797 A

(51) Int. Cl.⁷ ............................................... B01D 15/08
(52) U.S. Cl. .................... 210/635; 210/656; 424/9.454; 564/153
(58) Field of Search ................................. 210/635, 656; 424/9.4, 9.454; 564/156, 153

(56) References Cited

U.S. PATENT DOCUMENTS

| 5,191,120 | A | * | 3/1993 | Kneller | 564/153 |
| 5,204,005 | A | * | 4/1993 | Doran | 210/656 |
| 5,489,708 | A | * | 2/1996 | Bailey | 564/153 |
| 5,550,287 | A | * | 8/1996 | Cannata | 564/153 |
| 5,811,581 | A | * | 9/1998 | Piva | 564/153 |
| 6,153,796 | A | * | 11/2000 | Malthe-Sorensen | 564/153 |

* cited by examiner

*Primary Examiner*—Ernest G. Therkorn
(74) *Attorney, Agent, or Firm*—Sughrue Mion, PLLC

(57) ABSTRACT

A process for the purification of water-soluble non-ionic contrast agents from water-soluble non-ionic impurities involves the steps of (a) injecting a raw water-soluble non-ionic contrast agent solution on a chromatographic column containing non-ionic resins; (b) eluting water-soluble impurities contained in the raw water-soluble non-ionic contrast agent solution with deionized water as a first eluent, and (c) eluting a water-soluble non-ionic contrast agent with alcohol as a second eluent.

5 Claims, No Drawings

PROCESS FOR THE PURIFICATION OF WATER-SOLUBLE NON-IONIC CONTRAST AGENTS

BACKGROUND OF THE INVENTION

1. Field of the Invention

The present invention relates in general to a method for purification of water-soluble non-ionic contrast agents. More particularly, the present invention relates to a process for the purification by chromatographic technique of water-soluble non-ionic contrast agents from a raw water-soluble non-ionic contrast agent solution.

2. Description of the Related Art

Water-soluble non-ionic contrast agents are usually used in medical treatment, especially in neurography, angiography, encephalography, enhanced computed tomography, and urography. As compared with the ionic contrast agent traditionally used in medical treatment, the non-ionic contrast agent has a lower incidence of side effects and complications.

However, the synthesizing steps of the non-ionic contrast agent are more complicated than those of ionic contrast agents, especially the purification step, because the non-ionic contrast agent cannot be purified from water solution by deposition like ionic contrast agents. Hence, removing the inorganic salts from the final reaction solution to enhance the yield of the product is the encountered problem.

The compound (s)—N,N'-bis(1,3-dihydroxyisopropyl)-5-lactylamido-2,4,6-triiodoisophthalamide (Iopamidol) is water-soluble. If Iopamidol is used for medical treatment, it must be purified after synthesis. However, Iopamidol's yield is not optimum. In CH 608189, Iopamidol is separated from the final reaction solution by alternating with cation exchange resin and anion exchange resin, and the yield is only 65%. In DE 19507294, Iopamidol is purified by alternating with strong base anion exchange resin and weak base anion exchange resin, and the yield is 82.7%. These methods cannot provide sufficient yield. If the yield is enhanced, costs are reduced.

SUMMARY OF THE INVENTION

The present invention provides a process for the purification of water-soluble non-ionic contrast agents using simple chromatographic technique. Yield is enhanced and costs are reduced.

The present invention provides a process for the purification of water-soluble non-ionic contrast agents from water-soluble non-ionic impurities. At first, a raw water-soluble non-ionic contrast agent solution is injected on a chromatographic column containing non-ionic resins. The deionized water acts as a first eluent, and a plurality of water-soluble impurities contained in the raw water-soluble non-ionic contrast agent solution are eluted with deionized water. The water-soluble non-ionic contrast agent is then eluted with alcohol.

DETAILED DESCRIPTION OF THE PRESENT INVENTION

In the present invention, the non-ionic contrast agent is synthesized using the method disclosed in Swiss patent No. 1,472,050 by Savac A. G. After iodination, acid chloride formation synthesis, chiral synthesis, amidation, and base hydrolysis, the obtained raw non-ionic contrast agent solution has numerous water-soluble impurities, including polar aprotic solvents, inorganic salts, water, and by-products. The polar aprotic solvent can be N,N-dimethyl acetamide (DMA) or N,N-dimethyl formamide (DMF). The solubilities in water of these impurities and the non-ionic contrast agent are similar. Therefore, it is difficult to obtain the non-ionic contrast agent by crystallization. In order to solve such problems, the present invention provides a separation method using non-ionic resin to effectively separate the water-soluble non-ionic contrast agent from water-soluble impurities.

In the present invention, the chromatographic column is packed with non-ionic resins, and then used to purify the water-soluble non-ionic contrast agent. The preferred non-ionic resins have favorable interaction with the water-soluble non-ionic contrast agent. The non-ionic resins can be polystyrene, polystyrene derivatives, polymethacrylate or polymethacrylate derivatives.

The raw water-soluble non-ionic contrast agent solution comprises water-soluble non-ionic contrast agents and water-soluble impurities. The water-soluble impurities include polar aprotic solvents, inorganic salts, water and by-products. At the first stage, deionized water acts as a first eluent and the raw water-soluble non-ionic contrast agent solution flows through the chromatographic column containing non-ionic resins. Because a strong interaction exists between the water-soluble non-ionic contrast agents and the non-ionic resins, the water-soluble non-ionic contrast agents stay in the chromatographic column. The other polar aprotic solvents, inorganic salts, water and by-products are then eluted out. At the second stage, alcohol acts as a second eluent so as to elute the water-soluble non-ionc contrast agent.

The process of the present invention is used for the purification of water-soluble non-ionic contrast agents from water-soluble non-ionic impurities. The water-soluble non-ionic contrast agent is a radiation ray contrast agent, such as:

(s)-N,N'-bis(1,3-dihydroxyisopropyl)-5-lactylamido-2,4,6-triiodoisophthalamide (Iopamidol);

N,N'-bis(2,3-dihydroxypropyl)-5-[N-(2,3-dihydroxypropyl)acetamido]-2,4,6,-triiodoisophthalamide (Iohexol);

N,N'-bis(2,3-dihydroxypropyl)-5-[N-(2-hydroxyethyl)-glycolamido]-2,4,6,-triiodoisophthalamide (Ioversol); and 5,5'-[malonylbis(methylimino)]bis[N,N'-bis[2,3-dihydroxyl-1-(hydroxymethyl)propyl]]-2,4,6-triiodoisophthalamide (Iotrolan).

The chromatographic column is packed with non-ionic resins. The non-ionic resins can be polystyrene, polystyrene derivatives, polymethacrylate, polymethacrylate derivatives, or other having strong interaction with the non-ionic contrast agents.

After the non-ionic resins are uniformly and closely packed into the chromatographic column, the deionized water flows through the chromatographic column to condition the non-ionic resins. Then the final reaction solution, that is, the raw water-soluble non-ionic contrast agent solution, is injected on the chromatographic column. An appropriate amount of deionized water is used to elute the impurities. With regard to the water-soluble non-ionic contrast agent, it is absorbed on the non-ionic resin in the chromatographic column.

The remaining water-soluble non-ionic contrast agent is eluted with alcohol having a low carbon number. The alcohol has great dissolving ability for the non-ionic contrast agent, and can be $C_{1-6}$ alcohol, such as methanol, ethanol, n-butanol, and iso-butanol.

After eluting with alcohol, the correcting eluate is treated by condensing, re-crystallizing et al. steps. The purity of the obtained non-ionic contrast agent is over 99.7%.

Without intending to limit it in any manner, the present invention will be further illustrated by the following examples.

EXAMPLE 1

In a reaction flask, 16.12 g of L-5-α-acetoxypropionylamino-2,4,6-triiodo-isophthalic acid di(1,3-dihydroxyisopropylamide) (which is the intermediate of Iopamidol) (19.7 mmol) was dissolved in 60 ml of 1N NaOH (60 mmol). After dissolving, the mixture reacted at room temperature for 2 hours. 3N HCl was added to the reactant mixture until the pH value reached 7. Water was added to the reactant mixture to 200 ml. The reactant mixture was injected on the 400 ml of SP207 column (produced by Mitsubishi, its solid phase is polystyrene derivative) which was full of water. 1600 ml of water flowed through the column, and the water flowed out of the column. The column was saturated with methanol. After removing the air in the column, 1300 ml of methanol flowed through the column at a flow rate of 200 ml/hr.

The eluate was collected, and 2 g of active carbon was added hereto. The eluate was stirred at room temperature for 20 min, and then washed with methanol, condensed and dried to obtain the viscosified fluid. The obtained viscosified fluid was 14.5 g the yield is 94.7%). The viscosified fluid was dissolved in 30 ml of methanol, and 120 ml of n-butanol was added. The mixture as stirred overnight at room temperature, and a solid was deposited. After filtering and drying overnight, the obtained solid was 13.11 g of Iopamidol. The purity, yield and $[\alpha]^{20}$ (in $H_2O$) of Iopamidol was 99.7%, 85.7%, and −4.88° (435 nm) respectively.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A process for the purification of water-soluble non-ionic contrast agents from water-soluble non-ionic impurities, which comprise polar aprotic solvents, inorganic salts and by-products, involves the steps of:

(a) injecting a raw water-soluble non-ionic contrast agent solution on a chromatographic column containing non-ionic resins;

(b) eluting water-soluble impurities contained in the raw water-soluble non-ionic contrast agent solution with deionized water as a first eluent; and (c) eluting a water-soluble non-ionic contrast agent with alcohol as a second eluent.

2. The method as claimed in claim 1, wherein the non-ionic resins are selected from the group consisting of polystyrene, polystyrene derivatives, polymethacrylate and polymethacrylate derivatives.

3. The method as claimed in claim 1, wherein the water-soluble non-ionic contrast agent is selected from the group, consisting of Iopamidol, Iohexol, Ioversol and Iotrolan.

4. The method as claimed in claim 1, wherein the alcohol is $C_{1-6}$ alcohol.

5. The method as claimed in claim 4, wherein the alcohol is selected from the group consisting of methanol, ethanol, n-butanol and isobutanol.

* * * * *